(12) United States Patent
Dorin et al.

(10) Patent No.: US 11,628,409 B2
(45) Date of Patent: Apr. 18, 2023

(54) CHARGED ISOPOROUS MATERIALS FOR ELECTROSTATIC SEPARATIONS

(71) Applicant: TeraPore Technologies, Inc., South San Francisco, CA (US)

(72) Inventors: Rachel Mika Dorin, South San Francisco, CA (US); Spencer William Robbins, South San Francisco, CA (US)

(73) Assignee: TeraPore Technologies, Inc., South San Francisco, CA (US)

( * ) Notice: Subject to any disclaimer, the term of this patent is extended or adjusted under 35 U.S.C. 154(b) by 100 days.

(21) Appl. No.: 15/538,600

(22) PCT Filed: Apr. 26, 2017

(86) PCT No.: PCT/US2017/029591
§ 371 (c)(1),
(2) Date: Jun. 21, 2017

(87) PCT Pub. No.: WO2017/189697
PCT Pub. Date: Nov. 2, 2017

(65) Prior Publication Data
US 2019/0039030 A1    Feb. 7, 2019

Related U.S. Application Data

(60) Provisional application No. 62/328,707, filed on Apr. 28, 2016.

(51) Int. Cl.
| | | |
|---|---|---|
| *B01D 71/82* | (2006.01) | |
| *B01D 67/00* | (2006.01) | |
| *B01D 69/02* | (2006.01) | |
| *B01D 71/80* | (2006.01) | |
| *C07K 1/22* | (2006.01) | |
| *C12N 9/36* | (2006.01) | |
| *B01D 71/28* | (2006.01) | |
| *B01D 71/26* | (2006.01) | |

(52) U.S. Cl.
CPC ......... *B01D 71/82* (2013.01); *B01D 67/0009* (2013.01); *B01D 67/0093* (2013.01); *B01D 69/02* (2013.01); *B01D 71/80* (2013.01); *C07K 1/22* (2013.01); *C12N 9/2462* (2013.01); *C12Y 302/01017* (2013.01); *B01D 71/26* (2013.01); *B01D 71/28* (2013.01); *B01D 2325/14* (2013.01); *B01D 2325/16* (2013.01)

(58) Field of Classification Search
CPC .... B01D 71/80; B01D 71/28; B01D 67/0009; B01D 67/0093; B01D 69/02; B01D 71/26; B01D 2325/14; B01D 2325/16; C07K 1/22; C12N 9/2462; C12Y 302/01017

See application file for complete search history.

(56) References Cited

U.S. PATENT DOCUMENTS

| | | | |
|---|---|---|---|
| 3,673,272 A * | 6/1972 | Dean ..................... | C08F 297/02 525/103 |
| 4,014,798 A * | 3/1977 | Rembaum .............. | B01D 69/08 210/500.23 |
| 4,399,035 A | 8/1983 | Nohmi et al. | |
| 4,666,991 A | 5/1987 | Matsui et al. | |
| 4,720,343 A | 1/1988 | Walch et al. | |
| 4,880,441 A | 11/1989 | Kesting et al. | |
| 5,114,585 A * | 5/1992 | Kraus ................ | B01D 67/0011 210/490 |
| 5,130,024 A | 7/1992 | Fujimoto et al. | |
| 5,158,721 A | 10/1992 | Allegrezza et al. | |
| 5,647,989 A | 7/1997 | Hayashi et al. | |
| 5,700,902 A | 12/1997 | Hancock et al. | |
| 5,700,903 A | 12/1997 | Hancock et al. | |
| 5,792,227 A | 8/1998 | Kahlbaugh et al. | |
| 5,805,425 A | 9/1998 | Peterson | |
| 5,907,017 A | 5/1999 | Ober et al. | |
| 5,928,792 A | 7/1999 | Moya | |
| 6,033,370 A | 3/2000 | Reinbold et al. | |
| 6,241,886 B1 | 6/2001 | Kitagawa et al. | |
| 6,354,443 B1 | 3/2002 | Moya | |
| 6,379,796 B1 | 4/2002 | Uenishi et al. | |
| 6,503,958 B2 | 1/2003 | Hughes et al. | |
| 6,565,782 B1 | 5/2003 | Wang et al. | |

(Continued)

FOREIGN PATENT DOCUMENTS

| | | |
|---|---|---|
| CA | 2886437 A1 | 5/2014 |
| CA | 3022510 A1 | 11/2017 |

(Continued)

OTHER PUBLICATIONS

Fink, Johannes Karl. Handbook of Engineering and Specialty Thermoplastics. 2011. vol. 2, Water Soluble Polymers. Chapter 7. p. 189-192. (Year: 2011).*
Qiu et al. "Selective Separation of Similarly Sized Proteins with Tunable Nanoporous Block Copolymer Membranes." ACS Nano. vol. 7, No. 1, 2013. p. 768-776 (Year: 2013).*
Phillip et al. (Nano Lett., 2011, 11, 2892-2900) "Tuning Structure and Properties of Graded Triblock Terpolymer-Based Mesoporous and Hybrid Films" (Year: 2011).*
Xiaoyan Qiu, et al. "Selective Separation of Similarly Sized Proteins with Tunable Nanoporous Block Copolymer Membranes". $^{ACS}$NANO., vol. 7, No. 1, pp. 768-776, 2013.
Yizhou Zhang, et al., "Microfiltration and Ultrafiltration Membrane Science and Technology". Journal of Applied Polymer Science, app. 41683, pp. 1-17, 2015.

(Continued)

*Primary Examiner* — Ryan B Huang
(74) *Attorney, Agent, or Firm* — Innovators Legal

(57) ABSTRACT

Multiblock polymer materials, methods of preparing, and using to separate proteins, nucleic acids, other biological or other biomolecules, compounds, or solutes, with high fluxes through electrostatic interactions where the self-assembled block polymer materials contain at least one of macro, meso, or micro pores, and at least some of the pores are isoporous, and at least one polymer block contains stationary electrostatic charge, or reactive functional groups to provide large surface areas that are charged in isoporous structure.

22 Claims, 13 Drawing Sheets

(56) References Cited

U.S. PATENT DOCUMENTS

| | | |
|---|---|---|
| 6,592,764 B1 | 7/2003 | Stucky et al. |
| 6,592,991 B1 | 7/2003 | Wiesner et al. |
| 6,663,584 B2 | 12/2003 | Griesbach, III et al. |
| 7,056,455 B2 | 6/2006 | Matyjaszewski et al. |
| 7,438,193 B2 | 10/2008 | Yang et al. |
| 7,927,810 B2 | 4/2011 | Togawa et al. |
| 8,025,960 B2 | 9/2011 | Dubrow et al. |
| 8,147,685 B2 | 4/2012 | Pritchard |
| 8,206,601 B2 | 6/2012 | Bosworth et al. |
| 8,294,139 B2 | 10/2012 | Marsh et al. |
| 8,939,294 B2 | 1/2015 | Moore et al. |
| 9,162,189 B1 | 10/2015 | Aamer et al. |
| 9,169,361 B1 | 10/2015 | Aamer |
| 9,193,835 B1 | 11/2015 | Aamer |
| 9,441,078 B2 | 9/2016 | Aamer |
| 9,469,733 B2 | 10/2016 | Aamer et al. |
| 9,527,041 B2 | 12/2016 | Wiesner et al. |
| 10,711,111 B2 | 7/2020 | Wiesner et al. |
| 10,912,868 B2 | 2/2021 | Ushiro et al. |
| 2003/0073158 A1 | 4/2003 | Ma |
| 2003/0171560 A1 | 9/2003 | Peters |
| 2003/0226818 A1 | 12/2003 | Dunbar et al. |
| 2004/0065607 A1 | 4/2004 | Wang et al. |
| 2004/0122388 A1 | 6/2004 | McCormack et al. |
| 2004/0126778 A1 | 7/2004 | Lemmens et al. |
| 2004/0129678 A1 | 7/2004 | Crowley et al. |
| 2004/0138323 A1 | 7/2004 | Stenzel-Rosebaum et al. |
| 2004/0242822 A1 | 12/2004 | Gawrisch et al. |
| 2006/0014902 A1 | 1/2006 | Mays et al. |
| 2006/0085062 A1 | 4/2006 | Lee et al. |
| 2006/0094598 A1 | 5/2006 | Simon |
| 2006/0151374 A1* | 7/2006 | Wu .................. A61L 2/0017 210/321.77 |
| 2006/0283092 A1 | 12/2006 | Chinone |
| 2007/0029256 A1 | 2/2007 | Nakano et al. |
| 2007/0265174 A1 | 11/2007 | Schlenoff |
| 2007/0287241 A1 | 12/2007 | Takahashi et al. |
| 2008/0097271 A1 | 4/2008 | Lo et al. |
| 2008/0193818 A1 | 8/2008 | Mays |
| 2008/0261255 A1 | 10/2008 | Tolosa et al. |
| 2009/0173694 A1 | 7/2009 | Peinemann et al. |
| 2009/0181315 A1 | 7/2009 | Spatz et al. |
| 2009/0208726 A1 | 8/2009 | Yang et al. |
| 2009/0209726 A1 | 8/2009 | Matsumoto et al. |
| 2009/0239381 A1 | 9/2009 | Nishimi et al. |
| 2010/0051546 A1 | 3/2010 | Vuong et al. |
| 2010/0108599 A1 | 5/2010 | Vizvardi et al. |
| 2010/0167271 A1 | 7/2010 | Ryan |
| 2010/0181288 A1 | 7/2010 | Tang et al. |
| 2010/0219383 A1 | 9/2010 | Eklund |
| 2010/0224555 A1 | 9/2010 | Hoek et al. |
| 2011/0130478 A1 | 6/2011 | Warren et al. |
| 2011/0240550 A1 | 10/2011 | Moore et al. |
| 2011/0275077 A1 | 11/2011 | James et al. |
| 2012/0048799 A1 | 3/2012 | Na et al. |
| 2012/0318741 A1 | 12/2012 | Peinemann et al. |
| 2013/0053748 A1 | 2/2013 | Cotton |
| 2013/0112613 A1 | 5/2013 | Kang et al. |
| 2013/0129972 A1 | 5/2013 | Xu |
| 2013/0193075 A1 | 8/2013 | Liang et al. |
| 2013/0344375 A1 | 12/2013 | Brant et al. |
| 2014/0005364 A1 | 1/2014 | Gottschall et al. |
| 2014/0217012 A1 | 8/2014 | Wiesner et al. |
| 2014/0363572 A1 | 12/2014 | Moll et al. |
| 2014/0371698 A1 | 12/2014 | Chang et al. |
| 2015/0151256 A1 | 6/2015 | Abetz et al. |
| 2015/0336058 A1 | 11/2015 | Hillmyer et al. |
| 2015/0343395 A1 | 12/2015 | Aamer et al. |
| 2015/0343398 A1 | 12/2015 | Aamer et al. |
| 2016/0023171 A1* | 1/2016 | Phillip .................. B01D 61/02 210/650 |
| 2016/0229969 A1 | 8/2016 | Wiesner et al. |
| 2016/0288062 A1 | 10/2016 | Ait-Haddou et al. |
| 2016/0319158 A1 | 11/2016 | Fleury et al. |
| 2016/0375409 A1 | 12/2016 | Stasiak et al. |
| 2017/0022337 A1 | 1/2017 | Wiesner et al. |
| 2017/0105877 A1 | 4/2017 | Buteux et al. |
| 2017/0327649 A1 | 11/2017 | Wiesner et al. |
| 2018/0043314 A1 | 2/2018 | Onyemauwa et al. |
| 2018/0043656 A1 | 2/2018 | Song et al. |
| 2019/0233307 A1 | 8/2019 | Fujimura et al. |
| 2020/0238227 A1 | 7/2020 | Dorin et al. |
| 2020/0339770 A1 | 10/2020 | Wiesner et al. |
| 2021/0040281 A1 | 2/2021 | Dorin et al. |

FOREIGN PATENT DOCUMENTS

| | | |
|---|---|---|
| CN | 201211329 Y | 3/2009 |
| CN | 101460203 A | 6/2009 |
| CN | 101516481 A | 8/2009 |
| CN | 101969902 A | 2/2011 |
| CN | 102224163 A | 10/2011 |
| CN | 102892486 A | 1/2013 |
| CN | 103797053 A | 5/2014 |
| CN | 104159657 A | 11/2014 |
| CN | 104768506 A | 7/2015 |
| CN | 105273211 A | 1/2016 |
| CN | 105536580 A | 5/2016 |
| CN | 106344539 A | 1/2017 |
| DE | 102012207338 A1 | 11/2013 |
| DE | 102014213027 A1 | 1/2016 |
| EP | 2160946 A1 | 3/2010 |
| EP | 2703016 A1 | 3/2014 |
| EP | 2705077 A2 | 3/2014 |
| EP | 2977101 A1 | 1/2016 |
| EP | 3056260 A1 | 8/2016 |
| EP | 3284529 A1 | 2/2018 |
| EP | 3541500 A1 | 9/2019 |
| EP | 3544720 A1 | 10/2019 |
| EP | 3658262 A1 | 6/2020 |
| FR | 3037071 A1 | 12/2016 |
| JP | 54-145766 A | 11/1979 |
| JP | 04-022428 A | 1/1992 |
| JP | H 09-048861 A | 2/1997 |
| JP | 2002-537422 A | 11/2002 |
| JP | 2005-500132 A | 1/2005 |
| JP | 2006-175207 A | 7/2006 |
| JP | 2011-117956 A | 6/2011 |
| JP | 2011-131208 A | 7/2011 |
| JP | 2011-189229 A | 9/2011 |
| JP | 2012-246162 A | 12/2012 |
| JP | 2015-083299 A | 4/2015 |
| JP | 2015-167914 A | 9/2015 |
| JP | 2016-514049 A | 5/2016 |
| JP | 2016-526089 A | 9/2016 |
| JP | 2017-153616 A | 9/2017 |
| JP | 2018-500401 A | 1/2018 |
| JP | 2019-514687 A | 6/2019 |
| KR | 10-2009-0088124 A | 8/2009 |
| KR | 10-2012-0047269 A | 5/2012 |
| KR | 10-2012-0124412 A | 11/2012 |
| KR | 2012-0124412 A | 11/2012 |
| KR | 10-2016-0020404 A | 2/2016 |
| KR | 10-2018-0019059 A | 2/2018 |
| SG | 10201706492V | 3/2018 |
| SG | 11201904425 Y | 6/2019 |
| SG | 11202000664 Y | 2/2020 |
| WO | WO 2005/082501 A1 | 9/2005 |
| WO | 2005/091755 A2 | 10/2005 |
| WO | 2008/034487 A1 | 3/2008 |
| WO | 2010/051150 A1 | 5/2010 |
| WO | 2011/098851 A1 | 8/2011 |
| WO | 2011/111679 A1 | 9/2011 |
| WO | 2011/123033 A1 | 10/2011 |
| WO | WO 2012/151482 A2 | 11/2012 |
| WO | 2014/164793 A2 | 10/2014 |
| WO | 2015/048244 A1 | 4/2015 |
| WO | 2015/168409 A1 | 11/2015 |
| WO | 2015/188225 A1 | 12/2015 |
| WO | 2016/023765 A1 | 2/2016 |
| WO | 2016/031834 A1 | 3/2016 |
| WO | 2016/066661 A1 | 5/2016 |
| WO | 2017/189697 A1 | 11/2017 |
| WO | 2018/043209 A1 | 3/2018 |

(56) References Cited

FOREIGN PATENT DOCUMENTS

| WO | 2018/055801 A1 | 3/2018 |
|---|---|---|
| WO | 2018/093714 A1 | 5/2018 |
| WO | 2018/097988 A1 | 5/2018 |
| WO | 2019/023135 A1 | 1/2019 |
| WO | 2019/178045 A1 | 9/2019 |
| WO | 2019/178077 A1 | 9/2019 |
| WO | 2019/195396 A1 | 10/2019 |

OTHER PUBLICATIONS

A.S. Devonshire et al., "Towards Standardisation of Cell-Free DNA Measurement in Plasma: Controls for Extraction Efficiency, Fragment Size Bias and Quantification." Anal. Bioanal. Chem., vol. 406, pp. 6499-6512, 2014.
S. Breitbach et al., "Direct Quantification of Cell-Free, Circulating DNA from Unpurified Plasma." PLOS One, vol. 9, Issue 3, e87838. pp. 1-11.
A. A. Shukla et al., "Recent Advances in Large-Scale Production of Monoclonal Antibodies and Related Proteins." Trends in Biotechnology, vol. 28, No. 5, pp. 253-261, 2010.
J. I. Clodt et al., "Carbohydrates as Additives for the Formation of Isoporous PS-b-P4VP Diblock Copolymer Membranes." Macromolecular Rapid Communications, vol. 34, 190-194, 2013.
S. P. Nunes et al., "From Micelle Supramolecular Assemblies in Selective Solvents to Isoporous Membranes." Langmuir, DOI 10.1021/la201439p, Jun. 28, 2011.
W. A. Phillip et al., "Tuning Structure and Properties of Graded Triblock Terpolymer-Based Mesoporous and Hybrid Films." Nano Letters, vol. 11, pp. 2892-2900, 2011.
S. Rangou et al., "Self-Organized Isoporous Membranes with Tailored Pore Sizes." Journal of Membrane Science, vol. 451, pp. 266-275, 2014.
H. Sai et al., "Hierarchical Porous Polymer Scaffolds from Block Copolymers." Science, vol. 341, pp. 530-533, Aug. 2, 2013.
H. Ahlbrecht et al., "Stereoselective synthesis." Methods of Organic Chemistry. Houben-Weyl, vol. E 21 a, 4th Edition Supplement, 1995.
R. van Reis et al., "High Performance Tangential Flow Filtration." Biotechnology and Bioengineering, vol. 56, No. 1, pp. 71-82, Oct. 5, 1997.
F. A. Carey, Organic Chemistry, Fifth Edition, pp. 859-860, 2003.
A Bruil et al., "The Mechanisms of Leukocyte Removal by Filtration." Transfusion Medicine Reviews vol. IX No. 2, pp. 145-166, Apr. 1995.
Behler, Ansgar (Edited by), "Poren," Rompp Verlag, Rompp online 4.0, Aug. 2005, retrieved from Internet: URL: https://roempp.thieme.de/roempp4.0/do/data/RD-16-03734.
Breiner et al., "Structural Characterization of the "Knitting Pattern" in Polystyrene-block-poly(ethylene-co-butylene)-block-poly(methyl methacrylate) Triblock Copolymers", Macromolecules 1998, 31, 135-141.
Clodt et al., "Performance study of isoporous membranes with tailored pore sizes", Journal of Membrane Science, vol. 495, Jul. 29, 2015, pp. 334-340.
D. Keskin, et al., "Postmodification of PS-b-P4VP Diblock Copolymer Membranes by ARGET ATRP." Langmuir, vol. 30, pp. 8907-8914, Jun. 19, 2014.
Dai et al., "Fabrication of 2D ordered structure of self-assembled block copolymers containing gold nanoparticles," Journal of Crystal Growth, vol. 288, No. 1, pp. 128-136, Feb. 2, 2006.
Doan Minh Y Nhi, "Investigation of the Effects of UV-Crosslinking on Isoporous Membrane Stability." KTH Chemical Science and Engineering, pp. 1-46, 2011.
E. Gifford et al., "Sensitivity Control of Optical Fiber Biosensors Utilizing Turnaround Point Long Period Gratings with Self-Assembled Polymer Coatings." Proceedings of the SPIE, vol. 6659 pp. 66590D-1-66590D-9 Sep. 30, 2007.
Hanselmann, Blockcopolymere, ROMPP Online, Version 3.37, Dokumentkennung RD-02-02007. Jul. 1, 2009.
Hilke et al., "Block copolymer/homopolymer dual-layer hollow fiber membranes", Journal of Membrane Science, vol. 472, Aug. 23, 2014, pp. 39-44.
Hoek et al., Physical-chemical properties, separation performance, and fouling resistance of mixed-matrix ultrafiltration member, Desalination, Elsevier, vol. 283, pp. 89-99. May 4, 2011.
Huang Yan et al: "Highly Ordered Mesoporous Carbonaceous Frameworks from a Template of a Mixed Amphiphilic Triblock-Copolymer System of PEO-PPO-PEO and Reverse PPO-PEO-PPO", Chemistry—An Asian Journal, vol. 2, No. 10, Oct. 1, 2007 (Oct. 1, 2007), pp. 1282-1289.
J. Suzuki et al., "Morphology of ABC Triblock Copolymer/Homopolymer Blend Systems." Journal of Polymer Science Part B: Polymer Physics vol. 40 pp. 1135-1141 Apr. 22, 2002.
Julie N.L. Albert et al. "Self-assembly of block copolymer thin films", Materialstoday, vol. 13, is. 6, Jun. 2010, pp. 24-33.
Jung et al., Structure Formation of Integral Asymmetric Composite Membranes of Polystyrene-block-Poly(2-vinylpuridine) on a Nonwoven, Macromolecular Materials and Engineering, vol. 297, No. 8, pp. 790-798. Feb. 9, 2012.
Kanegsberg, "Washing, Rinsing, and Drying: Items to Consider for the Optimization of Your Cleaning Process," https://www.materialstoday.com/metal-finishing/features/washing-rinsing-and-drying-items-to-consider-for/, Sep. 1, 2005. p. 2, paragraph 6.
Karunakaran et al. "IsoporousIPS-b-PEO ultrafiltration membranes via self-assembly and water-induced phase separatioln" Journal of Membrane Science, vol. 453 Issue 1 (Nov. 16, 2013): pp. 471-477.
Khademi, M. Application of Tubular Crssflow Microfiltration in Harvesting Microalgae. LSU Master's Theses. 2014, pp. 39-43.
Kharitonov et al., "Surface modification of polymers by direct fluorination: A convenient approach to improve commercial properties of polymeric articles," Pure Appl. Chem., vol. 81, No. 3, pp. 451-471, 2009.
Laboratory-Equipment.com, "Applications for Laboratory Ovens Across the Sciences." https://www.laboratory-equipment.com/blog/all-laboratory-equipment-blogs/applications-for-laboratory-ovens-across-the-sciences/, Oct. 15, 2015, p. 1, section "Standard and Specialized Lab Oven Applications".
Lawrence E. Nielsen, "Cross-Linking-Effect on Physical Properties of Polymers." Journal of Marcomolecular Science Part C, vol. 3(1), pp. 69-103, 2008.
Li Yuk Mun et al: "Asymmetric Membranes from Two Chemically Distinct Triblock Terpolymers Blended during Standard Membrane Fabrication", Macromolecular Rapid Communications, vol. 37, No. 20, Oct. 1, 2016 (Oct. 1, 2016), pp. 1689-1693.
Lubomir et al., "Deposition of polymeric perfluored thin films in proton ionic membranes by plasma processes," Applied Surface Science, vol. 254, pp. 173-176, 2007.
Mu X. et al., Nano-porous Nitrocellulose Liquid Bandage Modulates Cell and Cytokine Response and Accelerates Cutaneous Wound Healing in a Mouse Model. Carbohydr Polym., Sep. 25, 2015, vol. 136, pp. 618-629.
N. Lefevre et al., "Self-Assembly in Thin Films of Mixtures of Block Copolymers and Homopolymers Interacting by Hydrogen Bonds." Macromolecules, vol. 43, No. 18, pp. 7734-7743 Aug. 17, 2010.
Parul Jain et.al., "Protein purification with polymeric affinity membranes containing functionalized poly (acid) brushes", Biomacromolecules, 2010, vol. 11, No. 4, 1019-1026.
Peinemann et al, "Asymmetric superstructure formed in a block copolymer via phase separation", Nature Materials, V6, Dec. 2007 (Peinemann NLP).
Radjabian, Polymer, 55 (2014), 2986-2997 (Year: 2014).
Ren et al, J. Am. Chem. Soc, 1998, 120, 6830-6831 (Year: 1998).
Roland et al., "Supplementary Information Block Copolymer/Homopolymer Dual-Layer Hollow Fiber Membranes Imaging and Characterization Lab and c Water Desalination", Aug. 23, 2014, pp. 1-3.
Shahkaramipour et al., "Membranes with Surface-Enhanced Antifouling Properties for Water Purification," Membranes, vol. 7, pp. 13, 2017.
Tiraferri et al., Binding Silver and Silica Nanoparticles to Polymeric Membrane Surfaces for Novel Anti-Biofouling Properties, ACS

(56) References Cited

OTHER PUBLICATIONS

Division Proceedings, Division of Polymer Chemistry, Meeting 242, Aug. 28-Sep. 1, 2011, Denver, CO, USA. Sep. 1, 2011.
Volker Abetz "Isoporous Block Copolmer membranes", Macromolecular Rapid Communications, vol. 36, No. 1, Nov. 29, 2014 (Nov. 29, 2014), pp. 10-22.
Wang Zhaogen et al: "Isoporous membranes with gradient porosity by selective swelling of UV-crosslinked block copolymers", Journal of Membrane Science, vol. 476, Feb. 1, 2015 (Feb. 1, 2015), pp. 449-456.
Y Nhi et al., "Investigation of the Effect of UV-Crosslin King On Isoporous Membrane Stability", Chemical Science and Engineering, vol. 46, Dec. 12, 2011.
Yizhou Zhang et al: "Nanoporous membranes generated from self-assembled block polymer precursors: Quo Vadis?", Journal of Applied Polymer Science, vol. 132, No. 21, Jun. 5, 2015.
Young et al., Robert J., Introduction to Polymers, Third Edition, CRC Press 2011, pp. 6-9 and 456-457.

* cited by examiner

CHARGED ISOPOROUS MATERIALS FOR ELECTROSTATIC SEPARATIONS

CROSS-REFERENCE TO RELATED APPLICATION

This application is a national stage of International Application No. PCT/US17/29591, filed on Apr. 26, 2017, which claims the benefit of U.S. provisional application number 62/328,707, filed Apr. 28, 2016, the contents of which are incorporated by reference herein in their entirety.

STATEMENT REGARDING FEDERALLY SPONSORED RESEARCH

This invention was made with government support under GM110996 awarded by the National Institutes of Health. The government has certain rights in the invention.

FIELD OF THE INVENTION

Multiblock polymer separators including an isoporous material, methods of preparing, and using to separate solutes through electrostatic interactions.

BACKGROUND OF THE INVENTION

Despite major progress in understanding protein expression, structure, and function, purification of proteins from complex mixtures remains problematic. Target molecules, often in cell culture fluid, also contain a large variety of extraneous or even adventitious components, e.g. host proteins, cell debris, DNA, viruses, and endotoxins, which add to the complexities of separation. Target proteins are often highly sensitive to environmental conditions and may be easily denatured or otherwise damaged.

Upstream technology can result in product titers greater than 5 g/L, and are driving the need for high throughput purification. Traditionally, biomolecule purification has relied heavily on chromatography, including affinity chromatography and ion-exchange columns. However, these chromatographic techniques are throughput limited and contribute extensively to the high costs of downstream bioprocessing.

Ultrafiltration (UF) is frequently used in later stages of downstream bioprocessing for protein concentration and formulation. For example, there are commercially available UF membranes, which are either tracked-etched or phase-inverted. Track-etched membranes have very uniform pores, enabling selective separations, but suffer from low throughput due to low pore densities. On the other hand, phase-inverted membranes allow much higher fluxes, but have non-uniform pores and cannot achieve selective separations. Due to flux limitations, track-etched membranes are used almost exclusively for bench-scale research, while phase-inverted membranes are used extensively in downstream biopharmaceutical processes. Phase-inverted membranes empirically exhibit a broad log-normal pore size distribution, necessitating a 6-10× difference in protein molar mass for effective fractionation. This pore size variation causes uneven flow patterns across the membrane, broadening breakthrough curves and diminishing media capacity.

Deficiencies in membrane structure and chemical functionality have largely limited their use to concentration and formulation steps. Thus, there is a need to improve protein purification methods for both lab-scale-up verification, and of course commercial-scale manufacturing of medically relevant proteins. Applicants have found that combining the unique tuning of the physical structure of isoporous materials with chemical functionality to facilitate and separate similarly sized solutes through electrostatic interactions, enables the production of isoporous, charged multiblock polymers material, e.g., films, membranes, sheets and tubes, that result in high-throughput and high-resolution separation applications, that overcome the limitations of the prior art.

Other biomolecule separations from complex mixtures can also be especially difficult. Nucleic acids, for example, can be isolated from whole blood for diagnostics. The isolation of DNA from whole blood is an especially challenging separation due to solutes of various length scales including red blood cells, proteins, and salts. One method of DNA isolation is using electrostatic interactions to isolate the negatively charged DNA from complex mixtures. Nevertheless, no effective membrane technology has been commercialized to isolate DNA from whole blood due to the difficulty of the separation through existing membrane technology. Applicants have found that the herein described invention enables the separation and concentration of nucleic acids from whole blood.

Charged porous materials are effective for the prevention of biofilm growth. For example, in using such materials as dressings for wounds, porous materials enable the passage of gaseous phase chemicals like water vapor, nitrogen, and oxygen. However, when biofilms grow they can inhibit wound healing. The charged porous materials described herein may be used to inhibit biofilm growth. In addition, the charged porous materials may be further functionalized with antimicrobial chemistries to further enhance wound healing properties and aid in wound care applications.

Chromatography column have also been used extensively to separate species based on various physical and chemical features, including charge and size, however, chromatography is limited in throughput and often expensive. The charged porous materials described herein may be used to separate solutes based on charge and size. For example, species bound to the membrane through electrostatic interactions may be detached from the membrane by passing a gradient of eluent through the material. In this way, a gradient separation may be performed. Alternatively, a selection of species may be detached from the membrane by passing an eluent of fixed composition through the membrane. The fixed composition being suitable for detaching the desired selection of species only. In this way, an isocratic separation may be performed. Further a series of elutions may be performed with each elution being of fixed composition suitable for detaching additional selections of species. In this way, a step elution may be performed.

There has been a strong interest in using the combined effects of charge and size to fractionate solutes including biomolecules. However, a major limiting factor in the further development of this promising approach is the non-uniform pore sizes of existing membrane platforms. FIG. 1 illustrates the problem due to pore size distribution. Regions of large pore size (5) transport more of the fluid flow than regions of smaller pore size (10) as indicated by the arrow (30) representing a larger portion of the flow than that represented by the arrow (35). Charged sites are rapidly filled with bound species in the large pore size regions allowing such species to escape from the membrane while smaller pore size regions continue to bind. Thus, the breakthrough of species targeted to bind occurs at a lower volume throughput than would occur if all the pores were of a uniform size.

Applicants have resolved this issue by enhancing pore size uniformity to reduce the spread of the log-normal pore size distributions of historical membrane platforms. For example, in one embodiment of the invented membrane, as shown in FIG. 2, a single layer of nearly identical pores (15) is formed on the downstream surface of the membrane. This layer contributes the majority of the resistance to flow which causes the flow to be distributed uniformly, as indicated by the equal sized flow arrows (20) and (25), regardless of the pore size distribution in the upstream portion of the membrane.

SUMMARY

The invention relates to filters/separators with an isoporous multiblock polymer material, collectively material, methods of preparing, and using to separate solutes including biomolecules through electrostatic interactions.

The charged, self-assembled block polymer material of the invention contain at least one of macro, meso, or micro pores, at least some of which are isoporous, where at least one polymer block contains stationary electrostatic charges, or reactive functional groups. The material has major, minor and interstitial regions, partially or quantitatively functionalized by the charged moiety on the functional group to produce a stationary charge on the material, to provide a large surface area that is charged and an isoporous structure for facile separations of proteins, nucleic acids, other biological or other biomolecules or solutes, with high fluxes.

The isoporous, charged, multiblock polymer material of the inventions includes at least blocks A, B and C having at least one of macro, meso, or micro pores, at least some of which are isoporous, where at least one polymer block contains stationary electrostatic charge, or reactive functional groups, and defined by formula $$A\text{-}B\text{-}C \quad (I),$$

$$A\text{-}B\text{-}C\text{-}B \quad (II),$$

$$A\text{-}B\text{-}C\text{-}D \quad (III),$$

$$A\text{-}B\text{-}C\text{-}B\text{-}A \quad (IV),$$

$$A\text{-}C\text{-}B\text{-}C\text{-}A \quad (V)$$

The multiblock polymer of the invention is generically defined as containing blocks A, B, C, $(X)_n$, where n=0-7, and X can be the same or different and is selected from, A, B, C, D, E, F or G. A suitable block for one of A, B, or C, is a low Tg block ($\leq 25°$ C.) with the proviso that when one of the blocks is a low Tg block, at least one other block is a high Tg block ($>25°$ C.). At least one block must have stationary charge, or reactive functional groups which can react to generate stationary charge. A suitable block for D, E, F, or G includes but is not limited to: poly(butadiene), poly (isobutylene), poly(butylene), poly(isoprene) poly(ethylene), poly(styrene), poly(methyl acrylate), poly(butyl methacrylate), poly(ethersulfone), poly(methyl methacrylate), poly(n-butyl acrylate), poly(2-hydroxethyl methacrylate), poly(glycidyl methacrylate), poly(acrylic acid), poly(acrylamide), poly(sulfone), poly(vinylidene fluoride), poly(n,n-dimethylacrylamide), poly(2-vinylpyridine), poly(4-vinylpyridine), poly(ethylene glycol), poly(propylene glycol), poly(vinyl chloride), poly(tetrafluoroethylene), poly(siloxane), poly(ethylene oxide), poly(propylene oxide), poly (n-isopropylacrylamide), poly(dimethylaminoethyl methacrylate), poly(amic acid), poly(dimethylsiloxane), poly (lactic acid), poly(isocyanate), poly(ethyl cyanoacrylate), poly(ethylene glycol methyl ether methacrylate), poly(acrylonitrile), poly(hydroxystyrene), poly($\alpha$-methylstyrene), poly(ethyleneimine), poly(styrene sulfonate), poly(allylamine hydrochloride), poly(pentafluorostyrene), poly(2-(perfluorohexyl)ethyl methacrylate).

The invention includes materials, such as, but is not limited to, supported or unsupported, in three-dimensional, membrane, film, sheet, tube, or helical or spiral configuration, where the material includes a functionalized isoporous block polymer with a charged moiety, and renders the material suitable for high through-put and charge-based separations.

The invention includes isoporous multiblock polymers possessing a stationary charge that facilitates solute separation based on both size and electrostatic characteristics of the solutes.

The invention includes functionalized separators with high fluxes for protein fractionation and isolation for analytical and industrial protein fractionation.

The invention relates to isoporous materials that: facilitate separation of similarly sized molecules, such as, proteins e.g. through electrostatic repulsion of one positively charge protein and one neutral protein, for protein production and analysis, biospecific molecules: including patient specific biomolecules, whether in the laboratory, scale-up or commercial environment.

The invention relates to isoporous materials that: facilitate separation of similarly sized proteins, methods of preparing and use, through electrostatic interactions; facilitate separation of nucleic acids through electrostatic interactions; facilitate separation of charged biomolecules through electrostatic interactions.

The invention relates to isoporous materials that: facilitate selective separation of matrix metalloproteinases through electrostatic interactions.

The invention relates to charged isoporous material of various configuration: three-dimensional, films, tubes, spirals, sheets, etc.

The charged isoporous material having selectivity of at least 10, and/or a permeability of 50 $Lm^{-2}$ $hr^{-1}bar^{-1}$ for electrostatically separating similarly size proteins with different charge states.

The invention includes materials of self-assembling multi-block polymers or self-assembling multi-block copolymers (MBP or BCP) with at least one chemically reactive functionalized polymer block that form hierarchically porous materials with high surface areas and uniform pore sizes, which are disclosed herein. The reactive regions of these isoporous materials are partially or quantitatively functionalized by the reaction of terminal or cross-linking agents with the reactive units to produce a stationary charge on the material, such that the degree of charge is at least 20% to 90%, e.g., at least 25%, 30%, 40%, 50%, 60%, 70%, 80%, or 90% of available reactive units.

Self-assembled multiblock copolymer charged material wherein the material has mesopores comprising a size of about 1-200 nm, and all unit sizes and ranges therebetween, and macropores comprising a size that is at least 50 nm or greater Disclosed are self-assembled multi-block, isoporous charged materials described herein that effectively separate a charged solute or solutes at hydraulic permeabilities >50 $Lm^{-2}$ $hr^{-1}bar^{-1}$, >100 $Lm^{-2}$ $hr^{-1}bar^{-}$, >200 $Lm^{-2}$ $hr^{-1}bar^{-}$. The dual separation methodologies of size-exclusion and charge-interaction drive high-throughput bioprocessing of proteins, nucleic acids, therapeutic compounds, or other molecules or compounds of interest.

Disclosed are self-assembled multiblock, isoporous charged materials with stationary positive charges, to separate similarly sized proteins through electrostatic repulsion of one positively charge protein and one neutral protein.

Disclosed are self-assembled multiblock, isoporous charged materials with stationary negative charges, to separate similarly sized proteins through electrostatic repulsion of one positively charge protein and one neutral protein.

Disclosed are self-assembled multiblock, isoporous charged materials with stationary positive charges, to separate nucleic acids through charge interactions.

Disclosed are self-assembled multiblock, isoporous charged materials with stationary positive charges, to separate biomolecules through charge interactions.

Disclosed are self-assembled multiblock, isoporous charged materials with stationary negative charges, to separate biomolecules through charge interactions.

The isoporous nature of the 5-100 nm size pores, and all unit sizes and ranges therebetween is especially beneficial to charge separations since all species coming in contact with the isoporous separation layer are forced experience the same electrostatic environment. If the pores are too polydisperse in size, it is possible for solutes to experience different charge environments e.g. pass through the center of a large pore without any charge separation effects since electrostatic charge interactions dramatically drop off as a function of distance. The high porosity, and in some cases hierarchical structure, contribute to a high surface area and thus large amount of charge available for separations. In operation with a bind and elute mechanism, this also provides a large binding capacity.

DETAILED DESCRIPTION

Figure 1:
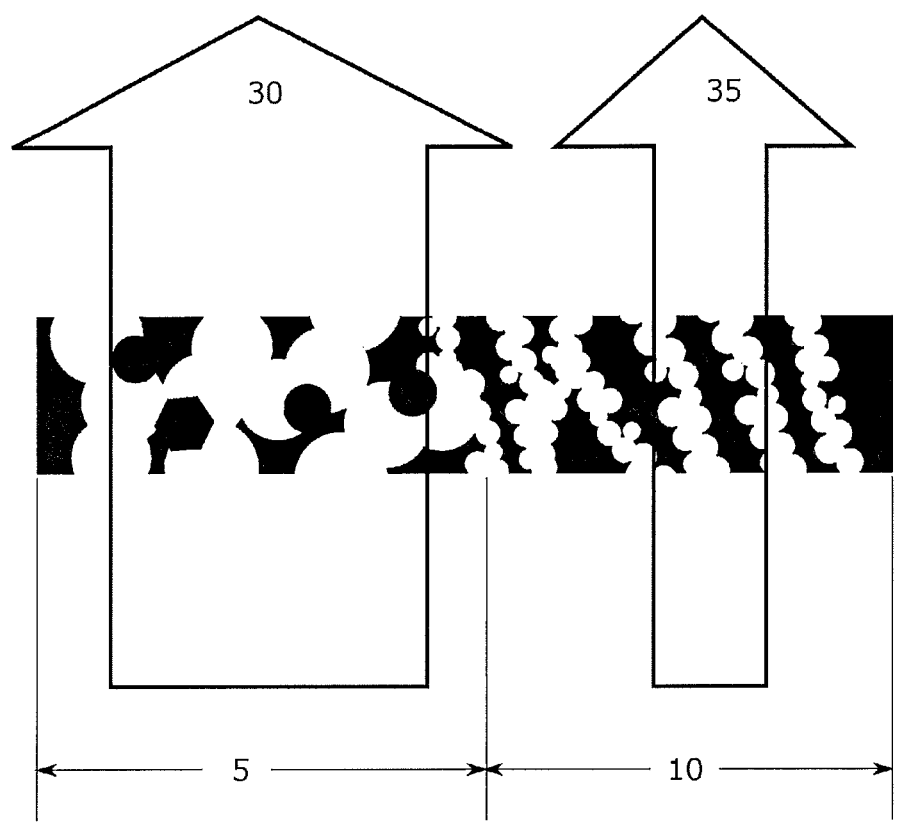
FIG. 1 is a schematic of the flow path through a membrane with a large pore size distribution. Flow in this structure results in inhomogeneous flow distribution. Regions of large pore size (5) transport more of the fluid flow than regions of smaller pore size (10) as indicated by the arrow (30) representing a larger portion of the flow than that represented by the arrow (35).
Figure 2:
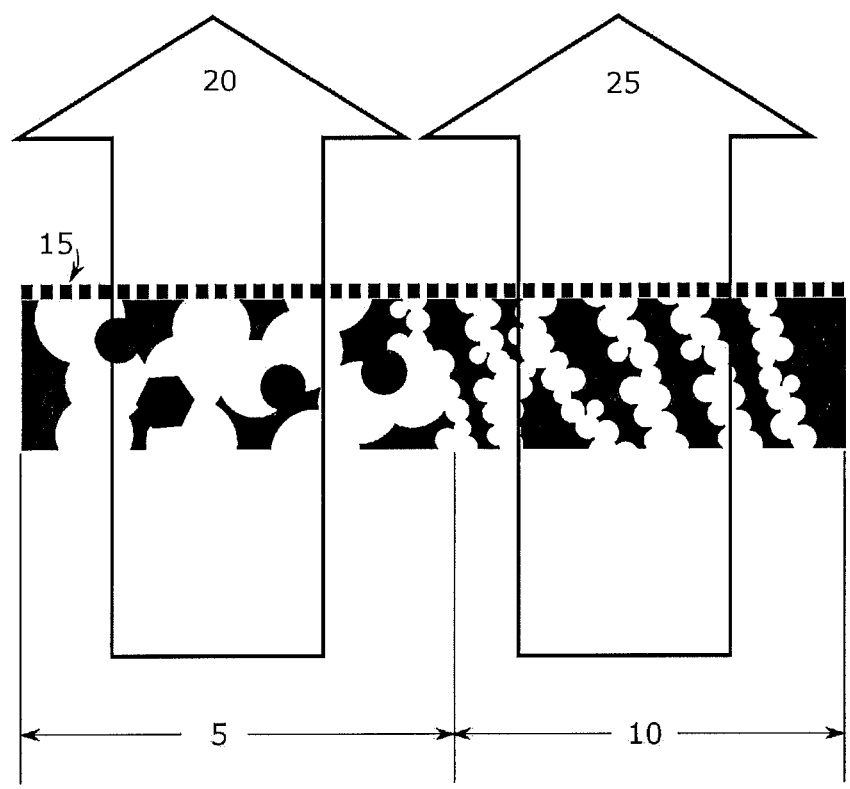
FIG. 2 is a schematic of the flow path through a membrane which includes a single layer of nearly identical pores (15), using the material of the invention described below, on the downstream surface of the membrane. This layer contributes the majority of the resistance to flow which causes the flow to be distributed uniformly, as indicated by the equal sized flow arrows (20) and (25), regardless of the pore size distribution in the upstream portion of the membrane.

In the following description, reference may be made to the accompanying drawings that form a part hereof, and in which is shown by way of illustration specific embodiments which may be practiced. These embodiments are described in detail to enable those skilled in the art to practice the invention, and it is to be understood that other embodiments may be utilized and that structural, logical and electrical changes may be made without departing from the scope of the present invention. The description of any example, embodiments or experimental procedures is, therefore, not to be taken in a limited sense.

The complexity of either or both the target molecules solutions and the target molecules themselves often require several steps and is a time consuming and expensive process, all exacerbated by the need to balance effective separation with high throughput. Two important performance parameters that will be improved through the chemical functionalization of isoporous membranes are the sieving coefficient, S is defined as:

$$S = \frac{C_P}{C_F}$$

where $C_P$ and $C_F$ are the concentration of the protein of interest in the permeate and feed, respectively, and the hydraulic permeability, $L_P$, defined as:

$$L_P = \frac{J_V}{\Delta P}$$

where $J_V$ is the volumetric filtrate flux and $\Delta P$ is the transmembrane pressure.

Separations involving nanoporous or ultrafiltration membranes have typically focused on size-selectivity, but electrostatic interactions have a significant impact on selectivity and permeability with protein solutes. The isoelectric point (pI) of a protein is the pH at which the biomolecule exhibits no net charge. In solutions below the pH of the protein pI, the molecule is positively charged, while at a pH above the protein pI, the molecule is negatively charged. Such charge characteristics have been exploited for protein filtration with nanoporous or ultrafiltration membranes by tuning solution pH as well as ionic strength, improving selectivity and throughput by up to an order of magnitude. Furthermore, there is a strong relationship between protein size and charge, with effective protein size increasing as ionic strength decreases due to decreased electrostatic shielding. More recently, combining processing conditions with charged nanoporous or ultrafiltration membranes has been shown to result in further improved protein selectivity.

One key differentiating feature of this invention over conventional charge-based membrane separations is the use of a focused pore distribution in isoporous membrane structure as opposed to nanoporous or ultrafiltration membranes with broad pore size distributions. This enables simplified processing conditions and higher operating pressures, which results in overall higher permeabilities.

Previous work on optimized charged ultrafiltration membrane separations in tangential flow configurations, in which the feed is passed parallel to the membrane surface, have resulted in average permeate fluxes of ~15-200 L m$^{-2}$ hr$^{-1}$ (Zydney and Kuriyel, *High-Performance Tangential Flow Filtration for Protein Separations. Downstream Processing of Proteins*, Springer, 35-46, (2000)). In contrast, self-assembled membranes of the present invention, with narrow "focused" pore size distributions show permeate fluxes up to 850 L m$^{-2}$ hr$^{-1}$.[9] While certain performance limiting factors are enhanced at high fluxes, e.g. concentration polarization and membrane fouling (Shukla and Thommes, *Trends Biotechnol.*, 28, 253-261, (2010)), the combination of physical membrane characteristics combined with electrostatic properties enables performance that surpasses existing membrane-based protein separations.

Suitable isoporous BCP material membranes for this invention are those that self-assemble. Typically, the preparation of such an isoporous organic membrane involves dissolving the BCP (or MBP) polymer in solvent(s) that are at least partially volatile, casting the solution under defined conditions so that at least a portion of the solvents are evaporated, and then contacting the resulting material, e.g., membrane/film with a phase separation solvent system. Such procedures are generally described in, for example, U.S. Pat. No. 5,700,902; U.S. Pat. No. 6,565,782; U.S. Patent Pub. No. 20110240550; U.S. Patent Pub. No. 20130193075; International Patent Pub. No. WO2005082501; U.S. Patent Pub. No. 20090173694; International Patent Pub. No. WO 2012/151482; EP2705077A2; Clodt et al, Macromol. Rapid Commun., 34, 190-194 (2013), Nunes et al, Langmuir, DOI 10.1021/Ia20439p, web published 28 Jun. 2011; Phillip et al, Nano Letters, 11, 2892-2900 (2011); and Rangou et al, J. Membrane Sci., 451, 22662-2275 (2014), the entirety of each incorporated by reference.

Another method for the formation of the porous membranes from suitable block polymers is the "SIM$^2$PLE" (spinodal decompostion-induced macro- and mesophase separation plus extraction by rinsing) process as described in Sai et al, Science, 341, 530 (2013). In this process, a suitable BCP is first prepared, mixed with a separate oligomeric polymer in a suitable organic solvent, casting the mixed solution to form a hierarchically porous membrane by partial solvent evaporation at an elevated temperature. At the final stage, the oligomeric polymer is removed from the resulting membrane (of the BCP) by rinsing. The thickness, pore size and structure of the membrane can be adjusted as desired by choice of solvent and polymer concentration, time and temperature of the solvent removal as well as other experimental factors. A suitable second oligomeric polymer for the "SIM$^2$PLE" process is one that is water-soluble and can be removed from the BCP by washing with water. In one embodiment, poly(acrylic acid) or PAA is used as the second oligomeric polymer although other soluble oligomeric polymers such as poly(ethylene oxide) PEO could be used as well.

In one embodiment, the block copolymers that self-assemble comprise a polymeric block that has a low Tg ($\leq 25°$ C.). This low Tg block provides mechanical toughness and eases processability and handleability of the material. Another block should have a Tg>25° C. which provides mechanical stability. At least one of the blocks should be a polymer that contains at least one functional group which can be chemically modified to introduce an electrostatic charge to the material, or is already charged.

In one embodiment, the functional polymer block contains an aromatic nitrogen heterocycle as the chemically modifiable functional group. In this embodiment, suitable aromatic heterocycles include, but are not limited to, pyridines, pyrazines, pyrimidines, pyridazines, quinolones, isoquinolines, quinoxalines, quinazolines, phenazines, isoxazoles, isothiazoles, imidazoles, benzimidazoles, triazoles, tetrazoles, and the like. Preferred aromatic nitrogen heterocycles are those that do not have an ionizable hydrogen on the nitrogen; that is, the nitrogen is fully part of an aromatic ring. Pyridine and its derivatives are particularly preferred heterocycles. Other examples of polymers that contain an aromatic heterocyclic group include, but are not limited to, poly(2-vinylpyridine) or poly(4-vinylpyridine) (P2VP or P4VP).

Figure 3:
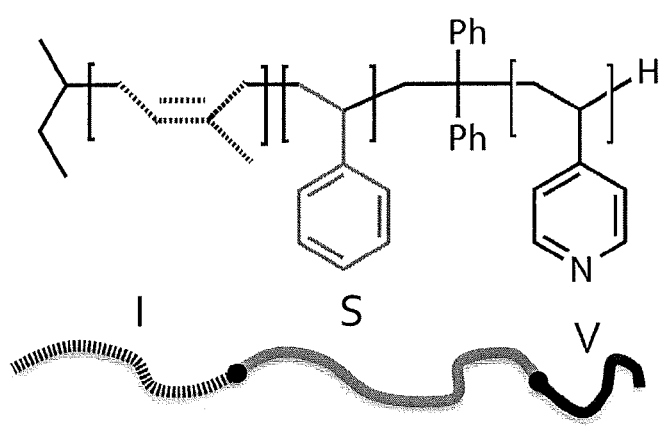
FIG. 3 is the chemical structure of triblock terpolymer ISV (poly(isoprene-b-styrene-b-4-vinylpyridine)) according to the invention. The poly(isoprene) block (I) is dashed, the poly(styrene) block (S) is grey, the poly(4-vinylpyridine) block (V) is black. The pyridine can be quaternized to introduce a positive charge on the V block.

In one embodiment of the invention, the blocks used to form the self-assembled isoporous material, e.g., membrane, is an ISV, a triblock or terpolymer poly(isoprene-b-styrene-b-4-vinyl pyridine), see the FIG. 3 showing blocks (I, S, V, which corresponds to the generic structure A-B-C)

In this embodiment, the triblock terpolymer architecture contains approximately 0.30 volume fraction polyisoprene (PI), 0.55 volume fraction polystyrene (PS), and 0.15 volume fraction poly(4-vinyl pyridine) (P4VP). The volume fractions of PI, PS and P4VP range from: $0.20 \leq PI \leq 0.40$ (e.g., block A); $0.45 \leq PS \leq 0.65$ (e.g., block B); $0.05 \leq P4VP \leq 0.35$ (e.g., block C). The material's architecture provides good mechanical properties while simultaneously allowing for small pore sizes. The ISV terpolymer starting material may be synthesized via anionic polymerization. In some embodiments, the isoporous (narrow pore size distribution) film has a surface layer (also referred to herein as a top layer) and a bulk layer. The suitable surface layers have a range of thicknesses. For example, the surface layer can have a thickness of from 5 nm to 500 nm, including all values to the nm and ranges therebetween. The surface layer has a plurality of pores extending thorough the depth of the surface layer. Pores size (e.g., diameter) in the surface layer ranges from 1 nm to 200 nm, including all values to the nm and ranges therebetween.

In an embodiment of the invention, the density of the surface pores of a membrane as described herein is at least $10^{14}$ pores/m$^2$, or at least $10^{15}$ pores/m$^2$. A narrow or focused pore size distribution (defined as the ratio of the maximum pore diameter to the minimum pore diameter (dmax/dmin)), is from 1 to 3, including all values to 0.1 and ranges therebetween.

In various examples, (dmax/dmin) is less than three, e.g., 1, 1.5, 2, 2.5, or 3, and all ranges thereof. For example, the film comprises a surface layer having nearly monodisperse mesopores. In an embodiment, the isoporous surface layer has a pore density of at least $1 \times 10^{14}$ pores/m$^2$ and a pore size distribution (dmax/dmin) of less than 3.

In some of the above embodiments, the P4VP material of the ISV terpolymer resides on the surfaces of the as-cast material matrix, as confirmed by both the pH dependent hydraulic permeability of the membranes that exhibit an inflection points near the pKa of P4VP, as well as stained transmission electron microscope images indicating nanometer-scale phase separation of each block.

Figure 4:
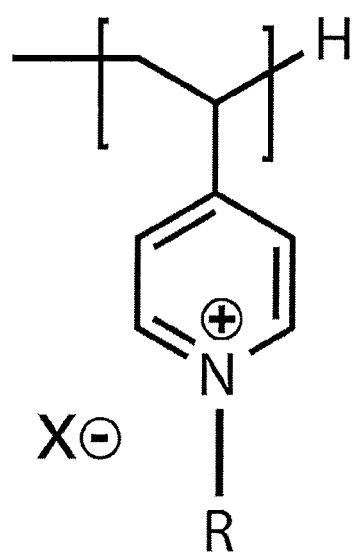
FIG. 4 is the chemical structure of a quaternized poly(4-vinylpyridine) where —R is any chemical group, as defined below, and X is a negative counterion.
Figure 5:
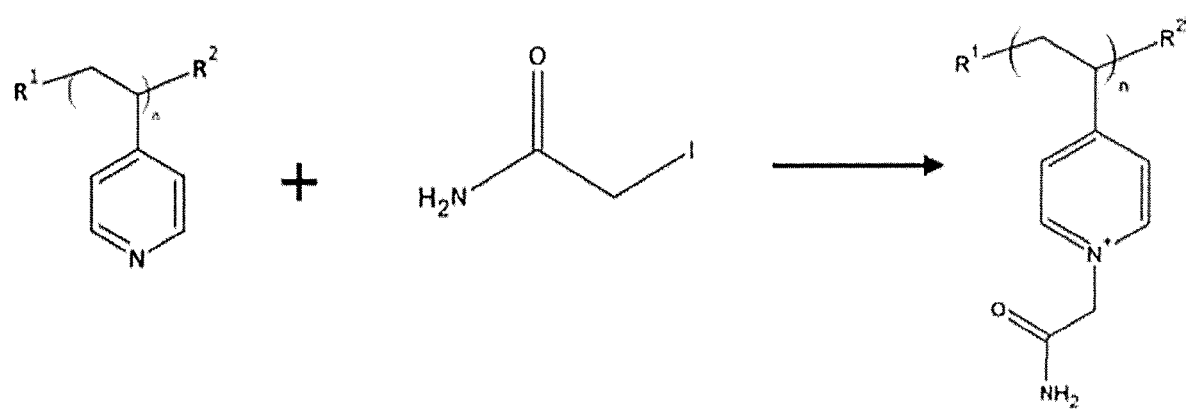
FIG. 5 is the chemical structures of poly(4-vinylpyridine) (P4VP) and iodoacetamide (left), which react to form iodoacetamide-quaternized P4VP with positively charged pyridinium and pendant amide group (right), according to the invention.
Figure 6:
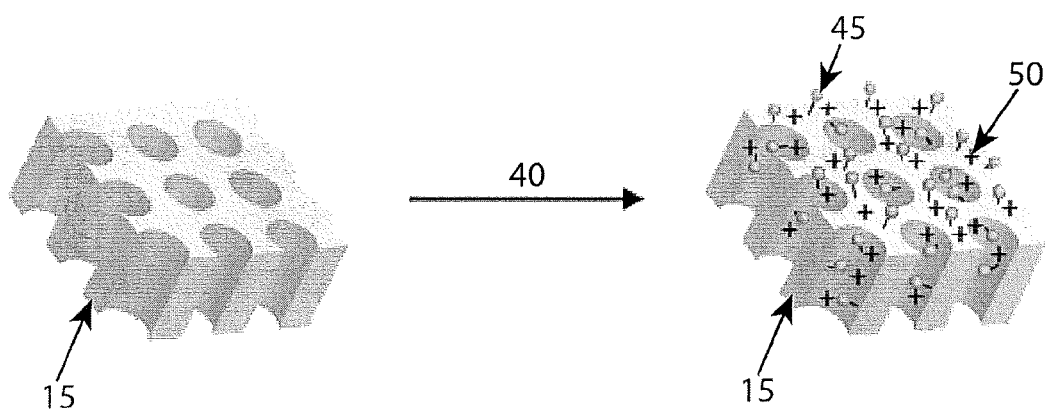
FIG. 6 is schematic of a material functionalization showing an untreated isoporous material (left), then a functionalized material (right) with attached chemical groups (spheres) and stationary positive charges ("+") on the isoporous material surface, according to the invention.
Figure 7:
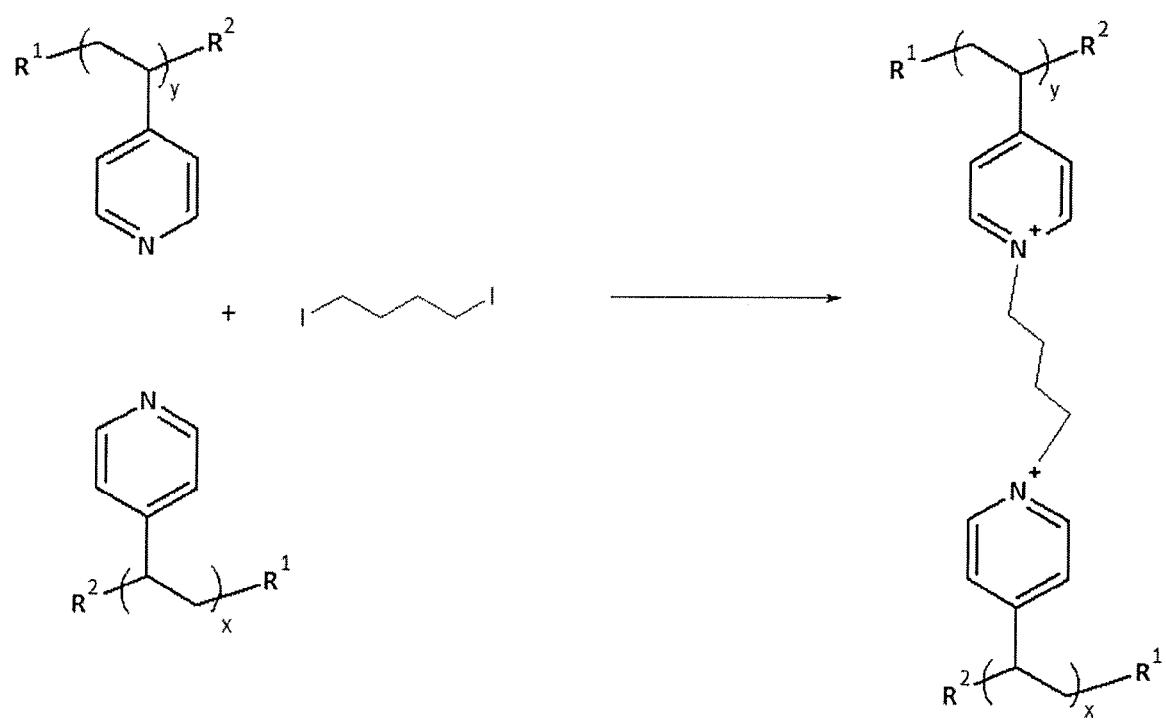
FIG. 7 is the chemical structures of multiple poly(4-vinylpyridine) (P4VP) units and diiodobutane (left), which react to form cross-linked P4VP (right), according to the invention.

The isoporous material, as described in some of the above embodiments (53-55), contains a polymer block with a nitrogen heterocycle that resides on the surfaces of the membrane and is accessible to quaternizing agents, which surfaces includes interstitial surfaces of the pores. For example, in the embodiment above where the copolymer contains P4VP (a weak base), the P4VP is quaternized using a variety of chemicals, resulting in a stationary positive charge on the membrane as shown in FIG. 4.

The quaternization agent in this embodiment is chosen to optimize the purification of the particular solute being targeted. There are many characteristics of the agent that can be applied in a useful way. For example, the degree of the hydrophilicity/hydrophobicity of the charged material can be an important consideration for some proteins. In order to control the hydrophilicity/hydrophobicity, the quaternization agent can be selected, for example, according to a value or range of C log P of the residue (a measurement that reflects the degree of hydrophilicity/hydrophobicity). For example, if a more hydrophilic environment is desirable, a quaternization agent such as iodoacetamide, iodoacetic acid, or crotonic acid which leaves a material with a relatively low C log P may be chosen. If a more hydrophobic environment is desirable, then a quaternization agent such as dodecyl iodide that leaves a material with a relatively high C log P may be chosen. There are other metrics of the degree of hydrophilicity/hydrophobicity other than C log P that may be used. For example, there may be an optimum value or range for the contact angle of the material after quaternization. The introduced functional groups (e.g. carboxylic acid, amide) may also be useful for subsequent chemical reactions or useful functionality (e.g. pH response, thermal response, solvent resistance).

The quaternizing agent in the above embodiment is any suitable compound that reacts with the nitrogen heterocycle of the BCP to form a positively charged heterocycle. One feature of the invention is that the degree or amount of charge can be varied in order to control the amount of positive charge. This allows for optimization of the total charge for the protein that is being purified. The charge density (corresponding to the degree of quaternization) of the membrane after quaternization can be determined by FTIR and NMR.

One group of quaternizing agents of the above embodiment are compounds defined by the formula R—X, where R is a $C_1$-$C_{24}$, more preferably $C_1$-$C_{20}$ substituted or unsubstituted, straight-chain, cyclic or branched alkyl or alkenyl group and X is a leaving group such as halide (F—, Cl—, I—, Br—), or —OSO$_2$CH$_3$, etc. Typically, the leaving group would be a terminal group (i.e. located on the end) on the alkyl or alkylene group and attached to an unsubstituted sp$^3$ carbon (i.e. —CH$_2$—X) in order to maximize reactivity. The alkyl or alkylene group may have 1-24 carbon atoms in the backbone. Examples of straight-chain alkyl groups would include, but are not limited to methyl, ethyl, butyl, hexyl, octyl, decyl and dodecyl. One example of a cyclic alkyl group is —CH$_2$-cyclohexane.

Examples of branched alkyl groups of the above embodiment are —CH$_2$—CH(CH$_3$)$_2$ and —CH$_2$CH$_2$—CH(CH$_3$)$_2$. An example of an alkenyl group would be geranyl (trans-3,7-dimethyl-2,6-octadien-1-X). An example of a substituted alkyl group would be benzyl (X—CH$_2$—C$_6$H$_5$). Although quaternization by a displacement reaction is preferred, it would be possible to quaternize the heterocycle by an addition reaction to a suitable olefin. For example, reaction with a H$_2$C═CHQ compound where Q is an electron-withdrawing group would result in a quaternized heterocycle of the form Het$^+$-CH$_2$-CHQ, where Q is an electron-withdrawing group. Examples of this class of agent would include ethyl methacrylate or methyl acrylamide.

Another class of quaternizing agents of the above embodiment is defined by the formula R—W—(R)—CH$_2$—X, where R is a $C_1$-$C_{24}$, more preferably $C_1$-$C_{12}$ substituted or unsubstituted alkyl, alkenyl or aryl group, W is a heteroatom such as oxygen, silicon, sulfur or nitrogen and X is a leaving group as above. Some examples of this class of quaternizing agent would be X—CH$_2$—O—C$_2$H$_5$, X—CH$_2$CH$_2$—O—CH$_3$ and X—CH$_2$CH$_2$-morpholine.

Another class of quaternizing agents is acyl compounds of the formula R—(W)—COCH$_2$—X where R is a $C_1$-$C_{24}$, more preferably $C_1$-$C_{10}$ alkyl or alkenyl, or $C_6$-$C_{10}$ aryl group, W is a heteroatom such as oxygen or nitrogen and X is a leaving group as above. Suitable examples of this class of acylation agents include X—CH$_2$—CO—C$_6$H$_5$, X—CH$_2$—CO$_2$CH$_3$, X—CH$_2$—CONH$_2$ and X—CH$_2$CON(CH$_3$)$_2$.

Suitable quaternization compounds of the above embodiments include, but are not limited to quaternization, including: bromobutane, bromo-PEG, bromopropionic acid, bromovaleric acid, chloroacetamide, chlorobutane, chlorobutyric acid, crotonic acid, diiodobutane, iodobutane, iodoacetamide, and iodopropionic acid. Iodoacetamide is of particular interest due to many desirable characteristics: low vapor pressure, relatively low hazard, inexpensive and readily available, water soluble, controllable quaternization, hydrophilicity, and preservation of the membrane's selective layer. These characteristics make this quaternization process easily scalable for large-scale production of electrostatically charged membranes. The final conditions used for quaternizing the membranes shown below were: 6.6 mM aqueous iodoacetamide, 60° C., 1h. The nucleophilic substitution reaction yields the positively charged pyridinium, with a pendant acetamide group in the material, as shown below:

In the above embodiment, the iodoacetamide reacts with poly(4-vinylpyridine) and yields the stationary charge on the membrane. This reaction results in a terminal amide on the membrane and a persistent positive charge.

Figure 8:
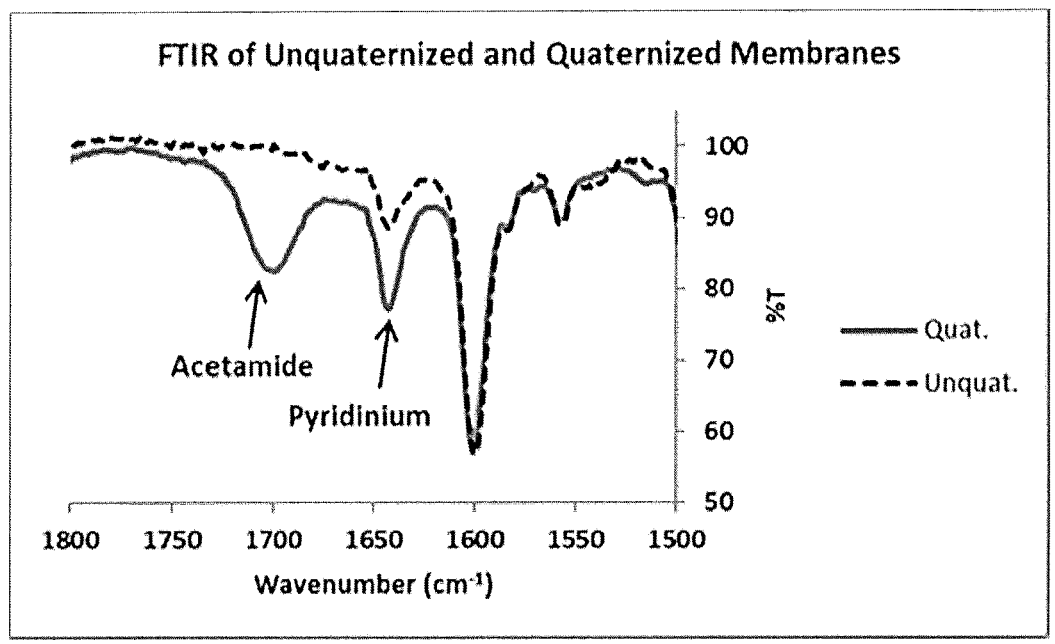
FIG. 8 is a FTIR characterization of unquaternized (top, dashed line) and quaternized (bottom, solid grey line) membranes, according to the invention. The characteristic increase at 1640 cm$^{-1}$ indicates the conversion of the heterocyclic amine to a charged pyridinium. The appearance of the band at 1700 cm$^{-1}$ derives from the amide C=O bond introduced during the quaternization.
Figure 9:
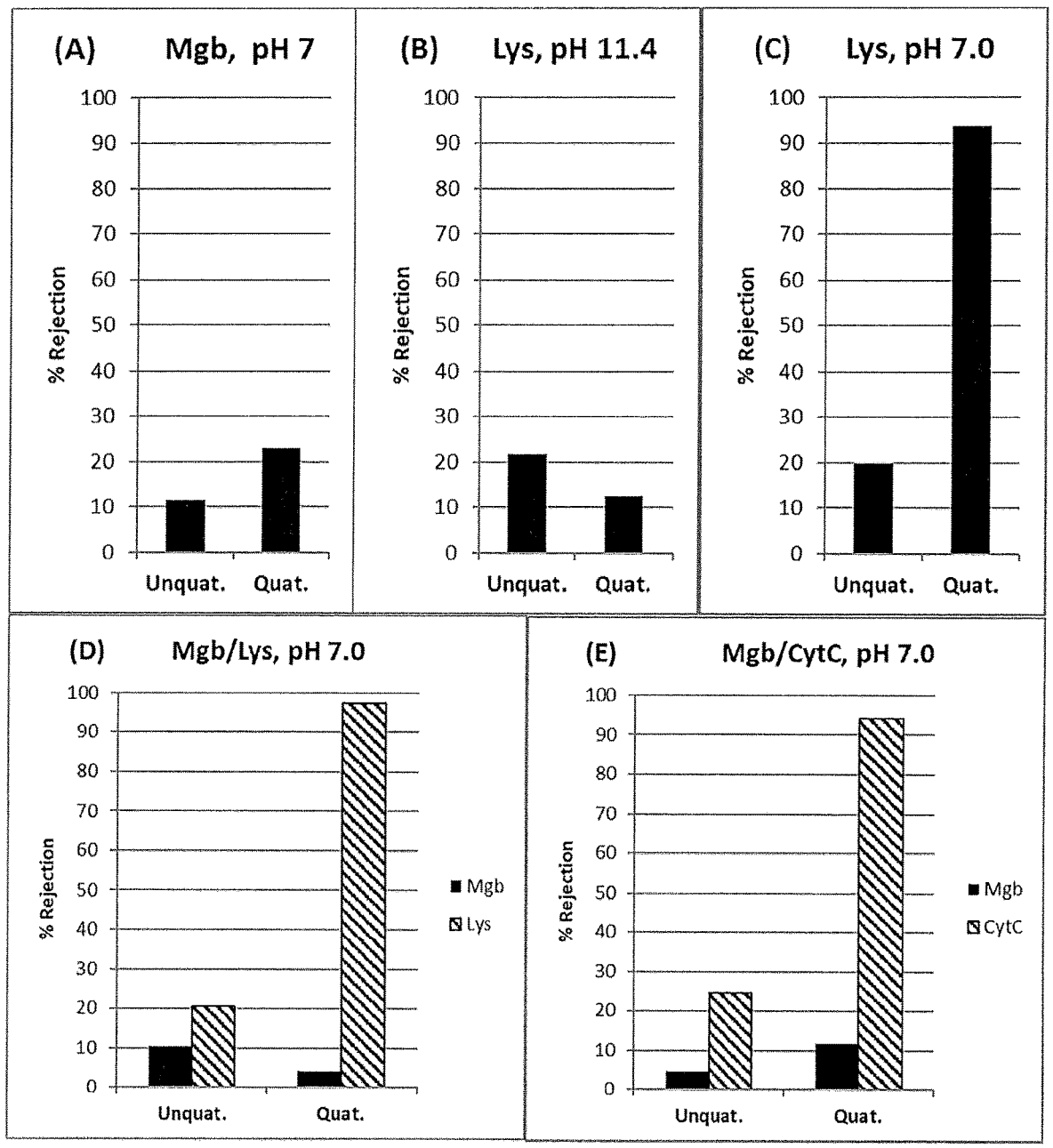
FIG. 9 is a graphical comparison of five charts, A-E illustrating the rejection behavior of single solute proteins (A)-(C) using unquaternized and quaternized membranes (black), and binary protein mixtures (D) and (E). Mgb is identified by solid black bars and whereas Lys and CytC are identified by hatched black and white bars. Protein solutions concentrations were 0.1 mg/mL.

Attenuated Total Reflection Fourier Transform Infrared Spectroscopy (ATR-FTIR) was used to characterize the unquaternized and quaternized membranes. Characteristic peaks for the quaternization process were observed in the iodoacetamide-treated membranes, as seen in FIG. 8. The characteristic increase at 1640 cm$^{-1}$ indicates the conversion of the heterocyclic amine to a charged pyridinium. The appearance of the band at 1700 cm$^{-1}$ derives from the amide C=O bond introduced during the quaternization. $^1$H Nuclear Magnetic Resonance (NMR) spectroscopy measurements showed 15.9% of the vinylpyridine protons did not change chemical environment—indicating a quaternization conversion of 84.1% using the standardized conditions. It is worth noting that similar experiments were performed for other chemical groups described above as well as for iodoacetamide treated membranes where temperature, reagent concentration, and reaction time were varied. While increasing the reaction time for iodoacetamide increased the peak intensities at 1640 cm$^{-1}$ and 1700 cm$^{-1}$, the one hour reaction was sufficient to convert a significant fraction of the 4-vinylpyridine monomers and convey highly charged characteristics to the membranes.

Suitable bifunctional quaternizing agents of the above embodiment, which have two sites of reaction with the heterocycle and serves as a cross-linking agent, include cross-linking agents defined by the formulas X—R—X, X—CH$_2$—CO—(W)—R—(W)—COCH$_2$—X or X—CH$_2$—(R)—W—(R)—CH$_2$—X, where R is an alkyl, alkenyl or aryl group, W is a heteroatom such as oxygen or nitrogen and X is a leaving group as above. The cross-linking agent may not be symmetrical; that is, one reactive group may be different from the second reactive group. Examples of a bifunctional quaternizing group include X—(CH$_2$)$_4$—X, X—CH$_2$CH$_2$—O—CH$_2$CH$_2$—X, ethylene glycol di(meth)acrylate, derivatives of methylenebisacrylamide and derivatives of N-1-hydroxyl-2,2-dimethoxyethyl acrylamide. A cross-linking agent such as 1, 4-diiodobutane is of particular interest due to the potential for increased membrane mechanical integrity and enhanced chemical resistivity.

Suitable quaternizing agents of the above embodiment also include additional functional groups that can bear positive or negative charges in order to adjust the overall charge of the material as well as the degree of the hydrophilicity/hydrophobicity. For example, the quaternization agent can be an anionic compound or a compound that ionizes to form an anion under the aqueous purification conditions. This would form a zwitterionic heterocycle that is neutral in overall charge and would reduce the positive charge of the material while still retaining highly polar characteristics. Examples of this kind of agent would include compounds with carboxylic or sulfonic acids groups such as —CH$_2$CH$_2$CO$_2$H or —CH$_2$CH$_2$SO$_3$H. Alternatively, the quaternization agent is a cationic compound or a compound that is protonated under the purification conditions. Examples of this kind would include —CH$_2$CONHCH$_2$CH$_2$—NH(CH$_3$)$_2$$^+$ or —H$_2$CH$_2$—N(CH$_3$)$_3$$^+$. This would increase the overall positive charge of the material. These kinds of charge control quaternization agents are used together with hydrophilicity/hydrophobicity control agents to control the membrane properties as required.

Since proteins and other kinds of biologic materials are often optically active, the functionalizing agent may be chiral. This would result in a material that has some degree of chirality associated with it. Examples of suitable optically active alkylation agents may be found in *Houben-Weyl Methods of Organic Chemistry Vol. E 21 a, 4th Edition Supplement, Stereoselective Synthesis*, H. Ahlbrecht et al, Ed., Thieme, 1995. For example, suitable chiral quaternization agents of the above embodiment would include optically active primary alkyl halides or mesylates.

Modification of the material to introduce charge is performed by immersing the as-prepared membranes in solutions containing the modification agent. In some embodiments, the charge introduction will be quantitative, >20%, >30%, >40%, >50%, >60%, >70%, >80%, or >90% of all available reaction sites, but in other embodiments, the degree of quaternization may be less than quantitative. A suitable solvent for the quaternization is water. However, some of the agents may have limited solubility in water, so combinations of water and an organic auxiliary solvent (such as an alcohol) are used. In some cases, it may be necessary to use a non-aqueous organic solvent or mixtures of organic solvents. Typical conditions for this process would be to dissolve the quaternization agent in an appropriate solvent system and treat the membrane at reagent concentrations of 2 and 100 mM, with a reaction time of 1 to 24 hours at a temperature of 20 to 30° C. In some cases with less reactive agents, it might be necessary to use longer reaction times and elevated temperatures. The progression of this process can be monitored using fourier transform infrared (FTIR) spectroscopy and nuclear magnetic resonance (NMR).

In some embodiments, the highest charge densities possible are desirable for the most selective charge-based separations of charged solutes. However, even in these cases, the membranes must retain high flux of the feed solutions at various pHs. Membrane performance can be measured utilizing a pressurized dead-end stirred-cell apparatus. This apparatus may use a 10 to 50 mL feed reservoir and membrane areas of ~4 cm$^2$ to ~13 cm$^2$.

The type or kinds of proteins or other biologically based materials to be purified or concentrated by the charged isoporous membrane of the invention is not limited. In particular, the feedstocks may be proteins derived from mammalian, bacterial, insect, viral or fungal cell lines. They are typically used in an aqueous feedstock, which may already been partially purified by another process. It is also possible to use fermentation broths as the feedstock. The feedstock may be whole blood, diluted blood, plasma, serum. The feedstock may contain nucleic acids, which may be separated using the material.

Three model proteins of interest include Myoglobin (Mgb), Lysozyme (Lys), and Cytochrome C (CytC). The typical molar masses and isoelectric points of these proteins are shown in Table 1, and they are representative of proteins that may be found in cell culture fluids. Flux with feeds containing protein solute can be measured using the same methods described above, while protein rejection can be quantitatively measured using UV-vis spectroscopy and aqueous high performance liquid chromatography (HPLC) on feed and permeate solutions. The calculated rejection, R, is related to the sieving coefficient as:

$$R = 1 - S = 1 - \frac{C_P}{C_F}$$

TABLE 1

Characteristics of standard similarly sized protein
molecules for charge-based separations.

| Protein | Isoelectric Point | MW (kg/mol) |
|---|---|---|
| Myoglobin (Mgb) | 7.0 | 16.7 |
| Lysozyme (Lys) | 11.4 | 14.3 |
| Cytochrome C (CytC) | 10.5 | 12.4 |

UV-Vis detection with HPLC is a simple and rapid method for separating protein mixtures and quantitatively determining protein concentrations.

However, in some embodiments of the invention, the feedstock may contain binary (or even more complex) solute mixtures, for example, the proteins Mgb/Lys or Mgb/CytC. One key performance parameter for such mixtures is the selectivity, $\Psi$, defined by van Reis and Saksena:

$$\Psi = \frac{S_1}{S_2}$$

where $S_1$ and $S_1$ are the sieving coefficients for lesser- and greater retained protein (van Reis and Saksena, J. Membrane Sci. 129, 19-29 (1997)). This parameter allows a simple and direct comparison of the relevant performance property between the charged and untreated membrane.

In this example, the Mgb/Lys and Mgb/CytC components are very similar in size and cannot be separated with simple ultrafiltration. Using the inventive membrane with either mixture at neutral pH, the Mgb is neutrally charged (due to its isoelectric point) and passes through the membrane with a selectivity corresponding to when Mgb is not in a mixture. The Lys or CytC are expected to be positively charged at neutral pH (due to their isoelectric points) and will be rejected by the like-charged membrane. The inventive membrane is designed to achieve selectivity between such membrane pairs of at least 10 in a dead-end system at flow rates of over 50 LMH/bar.

TABLE 2

Tabulated results of rejection, flux, and selectivity for Mgb/Lys
and Mgb/CytC protein pairs on unquaternized and quaternized
ISV membranes. The results show charge rejection of positively
charged proteins with the quaternized membranes. High selectivities
>10 are observed in the protein mixtures where one protein
is positively charged and the other is neutral.

| | % Rej | Permeability (LMH/bar) |
|---|---|---|
| Unquaternized Membrane, mixed solutes Mgb/Lys, pH 7.0 | | |
| Mgb | 10.3 | 1123 |
| Lys | 20.4 | |
| Quaternized Membrane, mixed solutes Mgb/Lys, pH 7.0 | | |
| Mgb | 4.2 | 54 |
| Lys | 97.4 | |
| Unquaternized Membrane, mixed solutes Mgb/CytC, pH 7.0 | | |
| Mgb | 4.6 | 1445 |
| CytC | 24.5 | |
| Quaternized Membrane, mixed solutes Mgb/CytC, pH 7.0 | | |
| Mgb | 11.8 | 65 |
| CytC | 94.2 | |

TABLE 2-continued

Tabulated results of rejection, flux, and selectivity for Mgb/Lys
and Mgb/CytC protein pairs on unquaternized and quaternized
ISV membranes. The results show charge rejection of positively
charged proteins with the quaternized membranes. High selectivities
>10 are observed in the protein mixtures where one protein
is positively charged and the other is neutral.

| | $\Psi_{Mgb/Lys}$ |
|---|---|
| Unquaternized membrane, mixed solutes Mgb/Lys | 1.20 |
| Quaternized membrane, mixed solutes Mgb/Lys | 36.85 |
| Unquaternized membrane, mixed solutes Mgb/CytC | 1.26 |
| Quaternized membrane, mixed solutes Mgb/CytC | 15.21 |

In some embodiments, the purification process using the charged isoporous membranes involves using pressurized buffered feed streams containing the biological material at, below, and above the isoelectric point of the desired material.

Figure 10:
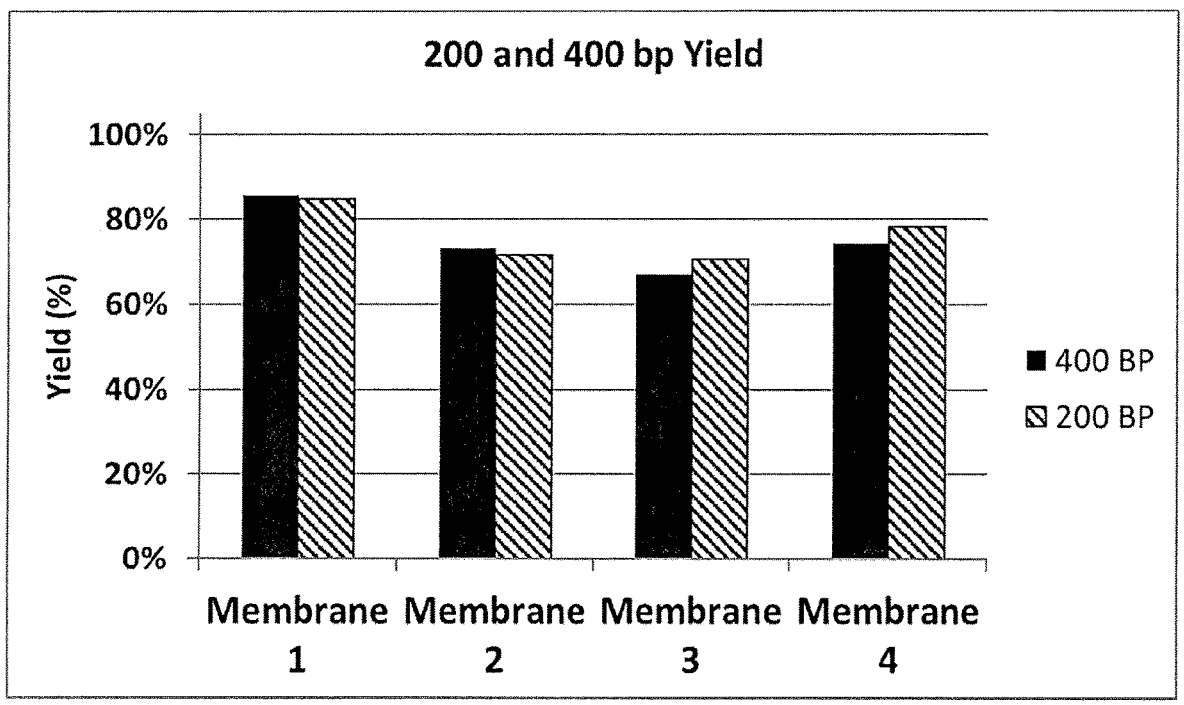
FIG. 10 is a graphical representation of 400 bp (black bars) and 200 bp (hatched black and white bars) DNA fragment yields bound to and eluted from four ISV membranes quaternized by iodoacetamide (materials of the invention), as described below.

In another embodiment, the charged isoporous material is used to isolate nucleic acids. After quaternization of P4VP of an ISV isoporous material, as in the above embodiments, the isoporous material has a positive charge. When exposed to a mixture of DNA fragments, the negatively charged DNA binds to the membrane. Subsequently, the DNA can be eluted from the membrane using a small amount of elution buffer solution. The recovery yields for 200 and 400 base pairs (bp) for four different membranes are shown in FIG. 10. The eluted DNA yield was quantified using gel electrophoresis, and 200 and 400 bp fragment yields, for four quaternized membranes. For 200 bp, yields varied from 71-85%, with a coefficient of variation (SD/mean) of 8.8%. The 400 bp yields were very similar, varying 67-86%, with a coefficient of variation of 10.6%. Relative to commercially available kits, which have relative standard deviations ranging from ~10% in the best cases to 49% for other commercial kits (Devonshire et al., Anal. Bioanal. Chem. 406, 6499-6512 (2014); Breitbach et al., PLOS ONE 9, e87838 (2014)), these results demonstrate very consistent and high DNA recovery using an extremely fast process with isoporous charged polymer materials.

Figure 11:
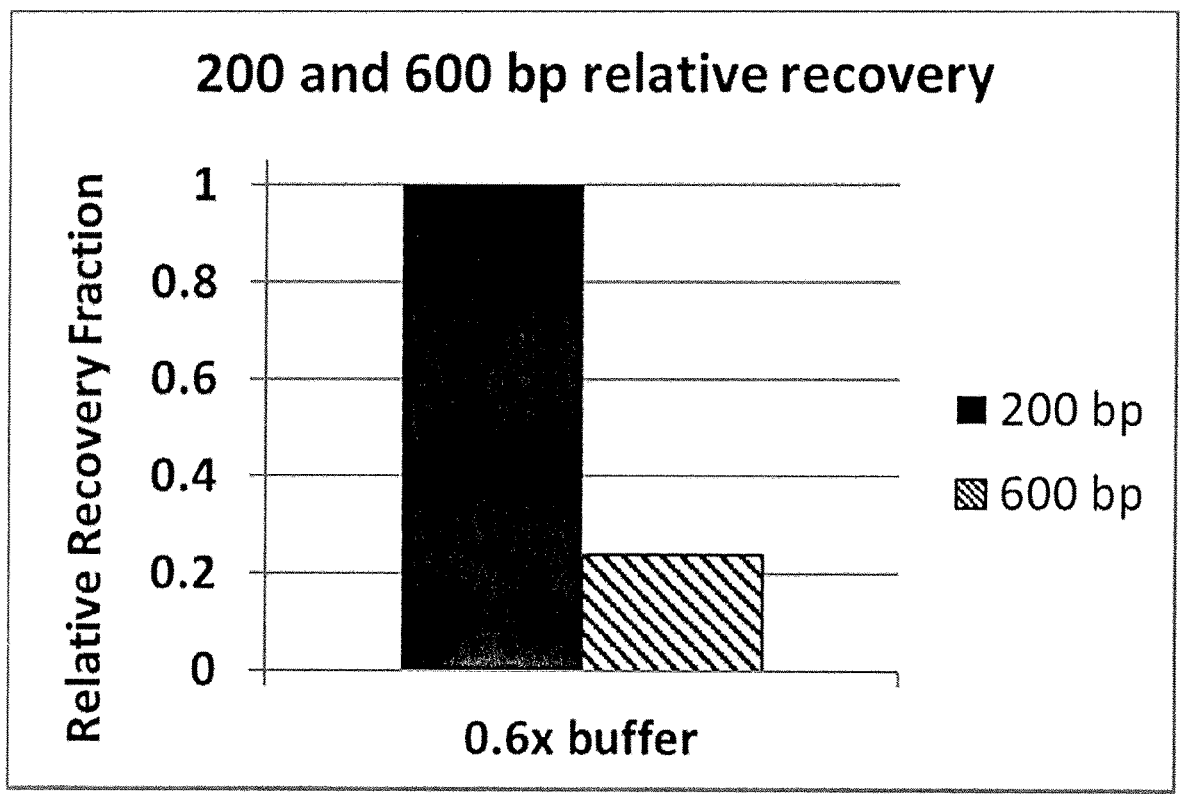
FIG. 11 is a graphical representation of relative recovery of 200 bp (black bar) and 600 bp (hatched black and white bar) DNA fragments eluted with 0.6× buffer, according to the invention.
Figure 12:
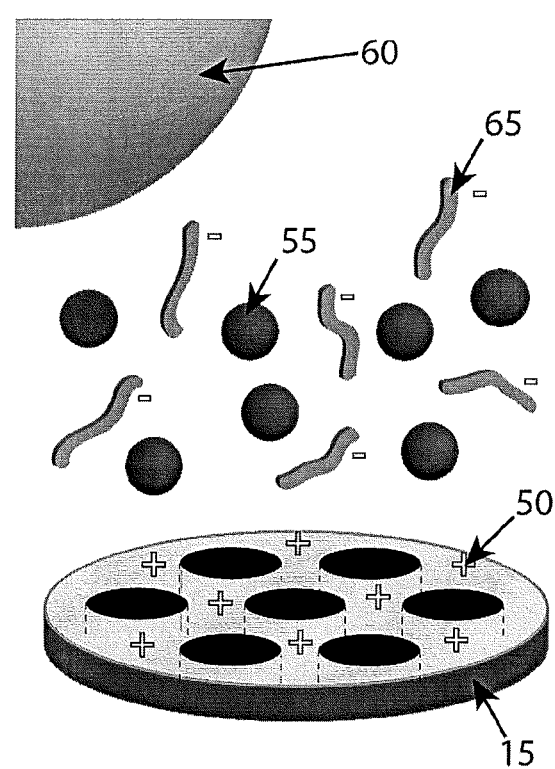
FIG. 12 is a schematic of layer of isoporous material (15) which is positively charged (50), challenged with a solution containing negatively charged nucleic acid fragments (65), small uncharged solutes and solvent molecules (55) and large cellular components (60), according to the invention. Non-nucleic acid components are passed through or retained by the membrane due to size-exclusion mechanisms and discarded, while the nucleic acid electrostatically binds to the membrane and subsequently size-selectively eluted.
Figure 13:
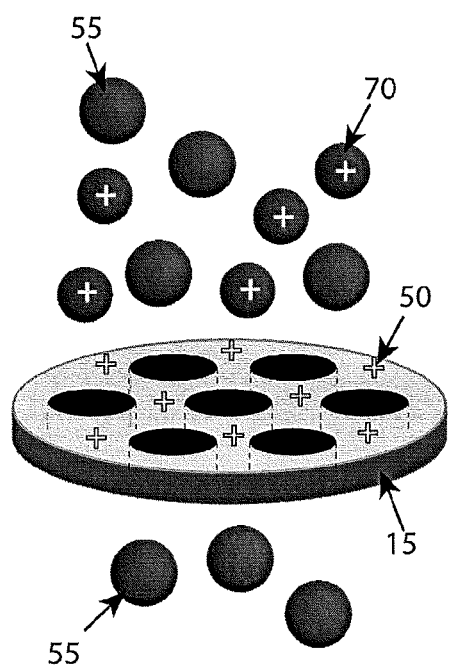
FIG. 13 is a schematic of isoporous material (15) which is positively charged (50), challenged with a solution containing positively charged molecules (70), small uncharged solutes and solvent molecules (55), according to the invention. Uncharged molecules are passed through or retained by the material due to size exclusion. Positively charged molecules are rejected due to charge repulsion.

In this embodiment, size-selective elution of DNA fragments is also possible. Different dilutions of elution buffer (0.6×, 0.3×) were used to elute. FIG. 11 shows the relative yields of the 0.6× buffer elution between the 200 and 600 bp fragments. The yield of the larger 600 bp decreased by over 4-fold, and all bands larger than 600 bp were not detectable, demonstrating that the charged isoporous membrane system can be used for DNA extraction, concentration, and size selection. At 0.3× buffer concentration even the 200 bp fragments were not eluted. These results show a powerful benefit of the charged membranes, which targets very specific DNA fragment sizes, and allows a single product to be used for numerous DNA isolation applications simply by tuning the elution conditions.

In another embodiment, the block copolymer is poly (styrene-b-isoprene-b-styrene-b-4vinylpyridine), corresponding to generic structure A-B-A-C. The P4VP is quaternized to generate stationary charge as in above embodiments. In some embodiments, the isoporous charged material is formed into a two-dimensional structure. In other embodiments, the isoporous charged material is formed into a three-dimensional structure.

In one embodiment, the reaction yielding stationary charge on the isoporous material changes the hydrophilicity of the material. In another embodiment, the reaction yielding the stationary charge on the isoporous material introduces a functional group to the material that can be used for further chemical reactions or material functionality.

In some embodiments, the stationary charge on the isoporous charged material is positive e.g. quaternized pyridine group, quaternized diethylaminoethyl group, quaternized dimethylaminoethyl group. In other embodiments, the stationary charge on the isoporous charged material is negative e.g. sulfonate group. In some embodiments, the isoporous material contains an amine group (e.g. pyridine, diethylaminoethyl, dimethylamino ethyl) which can be quaternized with a chemical agent to generate positive charge on the material. In one embodiment, amines are quaternized with a monofunctional alkylating agent, with one halogen selected from iodine, chlorine, and bromine e.g. 2-iodoacetamide, 2-bromoethanol. In one embodiment, the monofunctional alkylating agent has the formula: R—X where R is a $C_1$-$C_{24}$ substituted or unsubstituted, straight-chain, cyclic or branched alkyl or alkenyl group and X is a halogen group.

In another embodiment, the monofunctional alkylating agent has the formula: R—W—(R)—$CH_2$—X where R is a $C_1$-$C_{24}$ alkyl, alkenyl or aryl group, W is a heteroatom such as oxygen, silicon, sulfur or nitrogen and X is a halogen group. In another embodiment, the monofunctional alkylating agent has the formula: R—(W)—$COCH_2$—X where R is a R is a $C_1$-$C_{24}$ alkyl, alkenyl or aryl group, W is a heteroatom such as oxygen or nitrogen and X is a halogen group.

In another embodiment, multiple amines are quaternized with a multifunctional alkylating agent with two or more halogens selected from iodine, chlorine, and bromine e.g. 1,4-diiodobutane.

In another embodiment, amines are quaternized with an alkylating agent containing at least one reactive double bond e.g. crotonic acid.

In some embodiments, more than one of the aforementioned amine-alkylating agents containing is used to introduce charge on the isoporous material.

In some embodiments, the degree of charge on the isoporous charged material is at least 20% to 90%. In other embodiments, the degree of charge on the isoporous charged material is ≤90% of all available units.

In one embodiment, the charged isoporous material is further treated or functionalized with an antimicrobial agent.

In some embodiments, the geometry and area of the isoporous material that contains a stationary charge is controlled. In some embodiments, the geometry and area of the charged region is patterned lithographically, or achieved by attaching a portion or portions of charge modified material to an unmodified material or another substrate, or patterned onto a portion or portions of the unmodified material through printing or extrusion.

In some embodiments, the isoporous charged material is used as a separation media. In some embodiments, the isoporous charged material is used to separate biomolecules from other biomolecules. In an embodiment, the target biomolecule is a protein. In another embodiment, the target biomolecule is a nucleic acid.

In some embodiments, the separation mechanism using the charged isoporous material as separation media includes a bind and elute mechanism where the target species is bound to the material by electrostatic interactions to isolate it, wherein the target species can be unbound from the material to recover the target species.

In some embodiments, the separation mechanism using the charged isoporous material as separation media includes a charge repulsion mechanism, a size selection mechanism, and/or a concentration mechanism.

In some embodiments, the separation mechanism using the charged isoporous material as separation media with a bind and elute mechanism also includes a chemistry selective or size selective elution.

In some embodiments, the charged isoporous material is used for gradient separation, isocratic separation, or step separation.

In some embodiments, the charged isoporous material is used as a dressing or bandage for a wound, or is used to modulate the growth a biofilm.

In some embodiments, the charged isoporous material is combined with more than one charged material and packaged in a device, or charged isoporous material is combined with uncharged isoporous material and packaged as a device.

In some embodiments, the charged material is packaged in a pleated pack, crossflow cassette, hollow fiber module, syringe filter, capsule, pipette tip, centrifuge tube, spiral wound module, or sensor device.

In another embodiment, the charged material is packaged as a flat sheet.

In some embodiments, the charged isoporous material is immobilized on a support material or integrated directly with a textile.

In one embodiment, more than one charged isoporous material is packaged together as a kit.

In another embodiment, more than one device incorporating the charged isoporous material is packaged together as a kit.

In another embodiment, at least one charged isoporous material is packaged with one or more chemical solutions to elute bound target species after binding.

| Table of features identified in Figures | |
|---|---|
| 5 | Region of large pore size |
| 10 | Region of small pore size |
| 15 | Layer of nearly identical pore sizes |
| 20 | Arrow indicating uniform flow |
| 25 | Arrow indicating uniform flow |
| 30 | Arrow indicating larger amount of flow |
| 35 | Arrow indicating smaller amount of flow |
| 40 | Functionalization reaction to introduce charge |
| 45 | Functional group introduced from functionalization reaction |
| 50 | Positively charged material |
| 55 | Uncharged solutes/solvent molecules |
| 60 | Large solute such as cellular debris |
| 65 | Negatively charged nucleic acid solute |
| 70 | Positively charged solute |

The invention claimed is:

1. A charged, self-assembled poly(isoprene-b-styrene-b-4-vinyl pyridine) triblock copolymer material for solute separations, the material comprising:
   a surface layer comprising a plurality of mesopores having a size of from 5 nm to 100 nm, wherein the mesopores are isoporous and have a pore size distribution from 1 to 3, wherein the pore size distribution is defined as the ratio of the maximum pore diameter to the minimum pore diameter;
   wherein at least a portion of the 4-vinyl pyridine block is quaternized to provide the material with a positive stationary charge wherein the degree of charge on the at least a portion of the 4-vinyl pyridine block is ≤90% of all available units; and wherein the material exhibits a hydraulic permeability of 50 to 200 $L·m^{-2}·hr^{-1}·bar^{-1}$ at a pH of 7.0.

2. The material of claim 1, wherein the material has an asymmetric structure or a symmetric structure.

3. The material of claim 2, wherein the material contains macroporous domains and mesoporous wall structures in a single, integral structure.

4. The material of claim 3, wherein the macroporous domains are continuous.

5. The material of claim 1, wherein the 4-vinyl pyridine block is quaternized by a functionalization reaction, and the functionalization reaction provides the positive stationary charge.

6. The material of claim 1, wherein the 4-vinyl pyridine block is quaternized by reacting the 4-vinyl pyridine block with a quaternizing agent defined by the formula R—X, where R comprises a $C_1$-$C_{24}$ substituted or unsubstituted, straight-chain, cyclic or branched alkyl or alkenyl group and X is a leaving group.

7. The material of claim 1, wherein the 4-vinyl pyridine block is quaternized by reacting the 4-vinyl pyridine block with a quaternizing agent having the formula R—W—(R)—$CH_2$—X, where R is a $C_1$-$C_{24}$ substituted or unsubstituted alkyl, alkenyl or aryl group, W is a heteroatom and X is a leaving group.

8. The material of claim 1, wherein the 4-vinyl pyridine block is quaternized by reacting the 4-vinyl pyridine block with a quaternizing agent of the formula X—R—X, where R is an alkyl, alkenyl, alkenyl or aryl group, and X is a leaving group.

9. The material of claim 6, wherein R—X is selected from a group consisting of 2-bromoethanol, bromobutane, bromo-PEG, bromopropionic acid, bromovaleric acid, chloroacetamide, chlorobutane, chlorobutyric acid, dodecyl iodide, iodobutane, iodoacetamide, iodoacetic acid and iodopropionic acid.

10. The material of claim 1, wherein the 4-vinyl pyridine block is quaternized by reacting the 4-vinyl pyridine block with crotonic acid.

11. A self-assembled, charged, A-B-C triblock copolymer material having a surface layer comprising a plurality of mesopores having a size of from 5 nm to 200 nm, wherein the mesopores are isoporous and have a pore size distribution from 1 to 3, wherein the pore size distribution is defined as the ratio of the maximum pore diameter to the minimum pore diameter are isoporous, wherein one polymer block of the triblock copolymer has a $T_g$ of ≤25° C.; and one polymer block of the triblock copolymer comprises an aromatic heterocycle that is quaternized to provide the material with a positive stationary charge, the aromatic heterocycle selected from the group consisting of pyridines, pyrazines, pyrimidines, pyridazines, quinolones, isoquinolines, quinoxalines, quinazolines, penazines, isoazoles, isothiazoles, imidazoles, benzimidazoles, triazoles, and tetrazoles; wherein the degree of charge on the one polymer block of the triblock copolymer that is quaternized is ≤90% of all available units.

12. The material of claim 11, wherein the aromatic heterocycle is quaternized by reacting the aromatic heterocycle with a quaternizing agent defined by the formula R-X, where R comprises a $C_1$-$C_{24}$ substituted or unsubstituted, straight chain, cyclic or branched alkyl or alkenyl group or a polyethylene glycol (PEG) and X is a leaving group.

13. The material of claim 11, wherein the aromatic heterocycle is quaternized by reacting the aromatic heterocycle with a quaternizing agent having the formula R—W—(R)—$CH_2$—X, where R is a $C_1$-$C_{24}$ substituted or unsubstituted alkyl, alkenyl or aryl group, W is a heteroatom and X is a leaving group.

14. The material of claim 11, wherein the aromatic heterocycle is quaternized by reacting the aromatic heterocycle with a quaternizing agent of the formula R—(W)—$COCH_2$—X where R is a $C_1$-$C_{24}$ alkyl or alkenyl, or $C_6$-$C_{10}$ aryl group, W is a heteroatom and X is a leaving group.

15. The material of claim 11, wherein the aromatic heterocycle is quaternized by reacting the aromatic heterocycle with a quaternizing agent of the formula X—R—X, where R is an alkyl, alkenyl, alkenyl or aryl group, and X is a leaving group.

16. The material of claim 12, wherein R—X is selected from a group consisting of 2-bromoethanol, bromobutane, bromo-PEG, bromopropionic acid, bromovaleric acid, chloroacetamide, chlorobutane, chlorobutyric acid, dodecyl iodide, iodobutane, iodoacetamide, iodoacetic acid and iodopropionic acid.

17. The material of claim 11, wherein the aromatic heterocycle is quaternized by reacting the aromatic heterocycle with crotonic acid.

18. The material of claim 11 wherein the polymer block having a Tg of ≤25° C. is a polyisoprene block; and the block comprising the aromatic heterocycle is a poly(2-vinyl pyridine) block or a poly(4-vinyl pyridine) block.

19. The material of claim 11, wherein the A-B-C triblock copolymer material is a poly(isoprene-b-styrene-4-vinyl pyridine) block and the material exhibits a hydraulic permeability of 50 to 200 $L·m^{-2}·hr^{-1}·bar^{-1}$ at a pH of 7.0.

20. A method of forming a charged, isoporous multiblock polymer material according to claim 11, comprising providing at least a portion of the polymer block comprising the aromatic heterocycle with a charged moiety.

21. A method of forming a charged, isoporous multiblock polymer material according to claim 11, comprising contacting the A-B-C triblock copolymer material with a chemical agent that reacts with the aromatic heterocycle to introduce a stationary charge.

22. A process of separating a target biomolecule from a mixture of other biomolecules or other solutes containing the target biomolecule comprising contacting the mixture with a material according to claim 11, and then separating and/or removing the target biomolecule.

* * * * *